US012458735B1

(12) United States Patent
Whitehead

(10) Patent No.: US 12,458,735 B1
(45) Date of Patent: Nov. 4, 2025

(54) BREAST PUMP CADDY FOR HOLDING, ORGANIZING AND CARRYING A BREAST PUMP ASSEMBLY

(71) Applicant: Mitchell Whitehead, Batavia, IL (US)

(72) Inventor: Mitchell Whitehead, Batavia, IL (US)

( * ) Notice: Subject to any disclaimer, the term of this patent is extended or adjusted under 35 U.S.C. 154(b) by 0 days.

(21) Appl. No.: 18/789,666

(22) Filed: Jul. 30, 2024

Related U.S. Application Data

(60) Provisional application No. 63/529,953, filed on Jul. 31, 2023.

(51) Int. Cl.
*A61M 1/06* (2006.01)
*B65D 25/10* (2006.01)
*B65D 25/28* (2006.01)

(52) U.S. Cl.
CPC ........... *A61M 1/062* (2014.02); *B65D 25/108* (2013.01); *B65D 25/2823* (2013.01)

(58) Field of Classification Search
CPC .... A61M 1/062; A61M 1/06; A61M 2209/06; A61M 2209/08; A45C 5/045; A45C 5/06; B65D 25/108; B65D 25/2823; A47L 15/505; A24C 5/06
USPC ..................... 206/223, 373; 604/74; 294/146
See application file for complete search history.

(56) References Cited

U.S. PATENT DOCUMENTS 4,796,758 A * 1/1989 Hauk ........................ F25D 3/08 206/545
5,839,771 A * 11/1998 DeMars .................. A47L 13/51 220/555
6,296,165 B1 * 10/2001 Mears .................... A45C 15/00 150/108
8,636,169 B2 * 1/2014 Sampaio ............ B65D 25/2891 220/756
9,010,569 B1 * 4/2015 Estrada ................. A61J 9/0615 220/592.2
10,252,858 B1 * 4/2019 Pearson ................ B65F 1/1431
2002/0170935 A1 * 11/2002 Annis ................... A61M 1/062 224/655
2006/0266667 A1 * 11/2006 Mendenhall ........... A45C 11/00 206/427
2007/0257041 A1 * 11/2007 Bramlage .............. A45C 13/02 220/507
2013/0277381 A1 * 10/2013 Franzone, Jr. .......... B65B 5/068 53/413
2017/0245730 A1 * 8/2017 Dunn ....................... A47L 19/04
2019/0209748 A1 * 7/2019 Analytis ................. A61M 1/06
(Continued)

*Primary Examiner* — Steven A. Reynolds
(74) *Attorney, Agent, or Firm* — Steven Ivy P.C.

(57) ABSTRACT

Disclosed is a device for the controlled organization, storage, and transportation of a breast pump (electric or manual) and its accessories. The device comprises two main components: a caddy base and a caddy handle, which are firmly attached to each other using mounting screws. The caddy base consists of a bottom plate and an attached wall, forming a basket-like shape designed to securely house the electric breast pump, preventing any movement. Attached to the exterior surface of the wall are two bottle holders designed to house breast milk collection bottles. The caddy handle, having left and right braces, incorporates tubing notches designed to hold tubing in place being routed from the electric breast pump through the tubing inlet and connects to the top backflow caps. The braces also incorporate cap hooks and shield hooks designed to hold two breast shields, two bottom backflow caps, and the top backflow caps.

5 Claims, 4 Drawing Sheets

BREAST PUMP CADDY FOR HOLDING, ORGANIZING AND CARRYING A BREAST PUMP ASSEMBLY

(56) References Cited

U.S. PATENT DOCUMENTS

| | | | | |
|---|---|---|---|---|
| 2020/0030506 | A1 * | 1/2020 | Paget | A61M 1/062 |
| 2020/0390947 | A1 * | 12/2020 | Simpson | A45C 3/00 |
| 2021/0147113 | A1 * | 5/2021 | Workman | B65D 55/16 |
| 2023/0398267 | A1 * | 12/2023 | Patterson | A61M 1/062 |

* cited by examiner

BREAST PUMP CADDY FOR HOLDING, ORGANIZING AND CARRYING A BREAST PUMP ASSEMBLY

BREAST PUMP CADDY FOR HOLDING, ORGANIZING AND CARRYING A BREAST PUMP ASSEMBLY

RELATED PATENT APPLICATION

The present Non-Provisional U.S. patent application claims priority under 35 U.S.C. § 119 (e) to U.S. Provisional Patent Application No. 63/529,953 tiled BREAST PUMP CADDY, filed on Jul. 31, 2023, the subject matter of which is incorporated herein by reference.

FIELD OF INVENTION

The present invention relates to the general field of medical devices, and its subcategory containing both manual and electric breast pumps.

BACKGROUND OF THE INVENTION

Breast pumps are devices that allow lactating mothers to extract milk from their breasts. They became popular in the late 20th century as more women entered the workforce and needed a convenient way to continue breastfeeding while being away from their babies. Breast pumps are used by placing a breast shield (a cone-shaped cup) over the nipple, which creates a seal. The device then creates a vacuum that mimics a baby's sucking to draw out the milk, which is collected in an attached bottle or bag.

The global breast pump market size was valued at USD 2.74 billion in 2022 and is projected to grow at a compound annual growth rate (CAGR) of 8.5% from 2023 to 2030. The electric pumps segment held the largest market share in 2022 and is expected to witness the fastest growth rate with a CAGR of 8.9% during the forecast period. Electric breast pumps are powered by a motor and supply suction through plastic tubing to a horn (breast shield) that fits over the nipple. They provide more suction, making pumping significantly faster, and allow for pumping both breasts simultaneously.

Although individual experiences vary, it is not uncommon to encounter challenges or frustrations when using commercially available breast pumps. The ease of using a breast pump can vary depending on the specific model and individual preferences. Most breast pumps require regular cleaning, proper assembly, and, most importantly, proper disassembly, which takes place upon completion of the milk pumping process. This process is quite cumbersome and frequently results in misplacement of accessories and spilling of the collected milk.

The electric breast pumps currently available on the market most commonly consist of a breast pump motor, tubing, backflow caps, breast shields, and storage bottles. However, none of the commercially available breast pumps come with organizers or any other device designed to help the end user quickly and effectively organize and put away various accessories without compromising hygiene, losing accessories, or spilling the collected milk.

The present invention, titled "Breast Pump Caddy for Holding, Organizing and Carrying a Breast Pump Assembly" ("Caddy"), addresses the above-defined problem. The Caddy is a device for controlled housing of a breast pump and its accessories. The device comprises two main components, namely the caddy base and the caddy handle. The device may be used for transporting and storing unused breast pumps. However, the most practical application of the device occurs shortly after the breast pump is used to remove and collect breast milk into storage bottles. Under these circumstances, the device provides a stable platform for holding the bottles containing breast milk and easily accessible hooks for the quick placement and reliable retention of the cumbersome breast pump accessories.

BRIEF SUMMARY OF THE INVENTION

The following is intended to be a brief summary of the invention and is not intended to limit the scope of the invention:

The presented invention is a device titled "Breast Pump Caddy for Holding, Organizing and Carrying a Breast Pump Assembly" ("Caddy" or "Caddy Assembly"). The Caddy is used for efficient organization and storage of the electric breast pump and its accessories. The Caddy comprises two main components, namely the caddy base and the caddy handle. The caddy base consists of a bottom plate and an attached wall. These two components form a basket-like shape designed to securely house the electric breast pump, preventing any movement. The breast pump does not have to be removed from the caddy when in use, as the power cord of the electric breast pump can be plugged or unplugged via the plurality of cord portals. The caddy base is firmly attached to the caddy handle using mounting screws. Specifically, the wall of the caddy base, has two mounting blocks: one designed to fit into the left connecting receptacle and the other into the right connecting receptacle. These components also contain mounting holes through which the mounting screws and their corresponding lock nuts are placed to ensure reliable connection. The caddy handle, in addition to having a handle grip, comprises the left handle brace and the right handle brace. Both the left and right handle braces incorporate tubing notches, which are designed to hold tubing that is routed from the electric breast pump via the tubing inlet into the top backflow caps. The top backflow caps are stored on the left and right cap hooks, which are attached to the left and right braces. The braces also contain left and right shield hooks designed to hold the two breast shields and the two bottom backflow caps. Attached to the exterior surface of the wall are two bottle holders designed to house two breast milk collection bottles. This is the most practical feature of the Caddy, as milk that is collected in the bottles is frequently spilled when the end-user tries to hold and manage multiple accessories after the collection process is completed, with the pump typically occupying nearby flat surfaces.

DESCRIPTIVE KEY

- 100—breast pump caddy for holding, organizing and carrying a breast pump assembly ("caddy" or "breast pump caddy assembly")
  - 110—caddy base
    - 111—bottom plate
    - 112—wall
      - 113—top surface
      - 114—external surface
      - 115—tubing inlet
      - 116—two mounting blocks
      - 117—plurality of power cord portals
      - 118—two bottle holders
    - 119—plurality of weight cutouts
  - 120—caddy handle
    - 121—handle grip
    - 122—left handle brace
      - 123—left cap hook 124—left tubing notches
125—left shield hook
126—left connecting receptacle
128—right handle brace
129—right cap hook
130—right tubing notches
131—right shield hook
132—right connecting receptacle
140—mounting holes
141—mounting screws and corresponding nuts (lock nuts)
200—breast pump assembly
201—electric breast pump
202—tubing
203—power cord
204—top backflow caps
205—two bottom backflow caps
206—two breast shields
207—two breast milk collection bottles

BRIEF DESCRIPTION OF THE DRAWINGS

The components shown in the drawings are not to scale. In the interest of clarity, some of the components might be shown in a generalized form and could be identified utilizing commercial designations. All components, including its essential features, have been assigned reference numbers that are utilized consistently throughout the descriptive process outlined herein.

DETAILED DESCRIPTION AND BEST MODE OF IMPLEMENTATION

Figure 1:
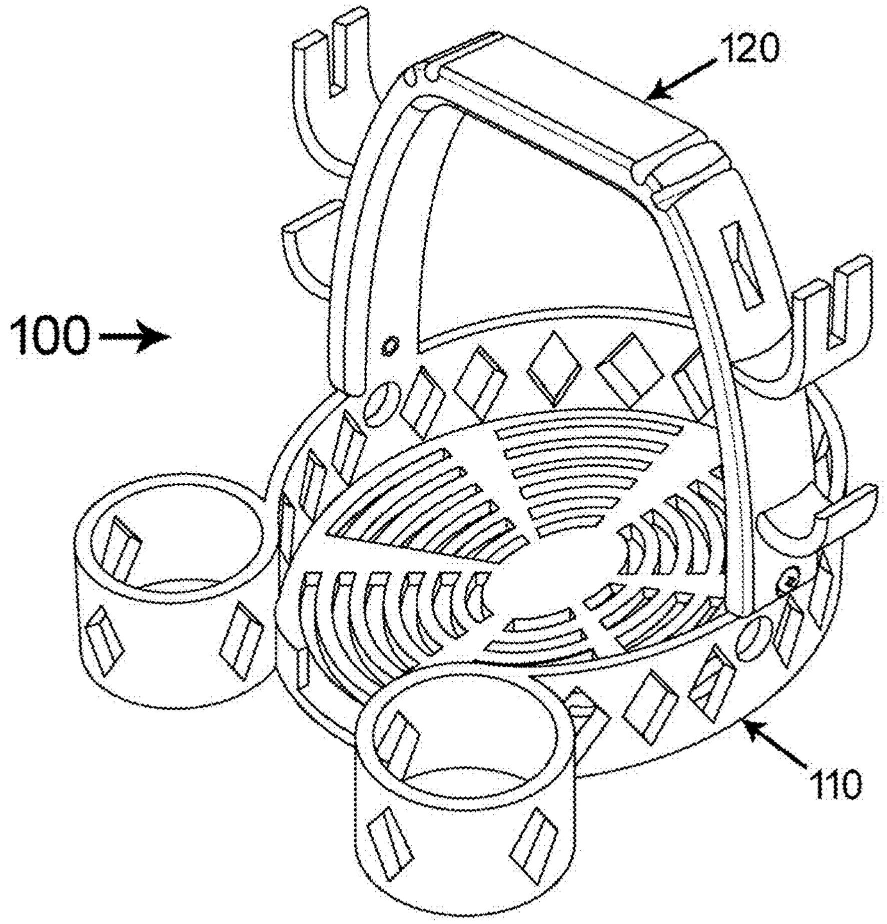
FIG. 1 is a right perspective view of the present invention, titled "Breast Pump Caddy for Holding, Organizing, and Carrying a Breast Pump Assembly" ("caddy" or "breast pump caddy assembly"). The figure shows the fully assembled caddy, with descriptive key numbers indicating the positions of its two primary components: (1) the caddy base and (2) the caddy handle; in accordance with an exemplary embodiment of the present invention.

The following description references to the above-defined drawings and represents only an exemplary embodiment of the invention. It is foreseeable, and recognizable by those skilled in the art, that various modifications and/or substitutions to the invention could be implemented without departing from the scope and the character of the invention:

As shown in FIG. 1, the presented invention is a device titled "Breast Pump Caddy for Holding, Organizing, and Carrying a Breast Pump Assembly" ("Caddy" or "Caddy Assembly"). The Caddy 100 is designed for the efficient organization and storage of the electric breast pump assembly 200 (i.e., electric breast pump and its accessories). The Caddy 100 may also be used for the storage, organization, and handling of non-electric or manually operated breast pumps of similar physical configuration. The Caddy 100 comprises two main components, namely the caddy base 110 and the caddy handle 120.

Figure 2:
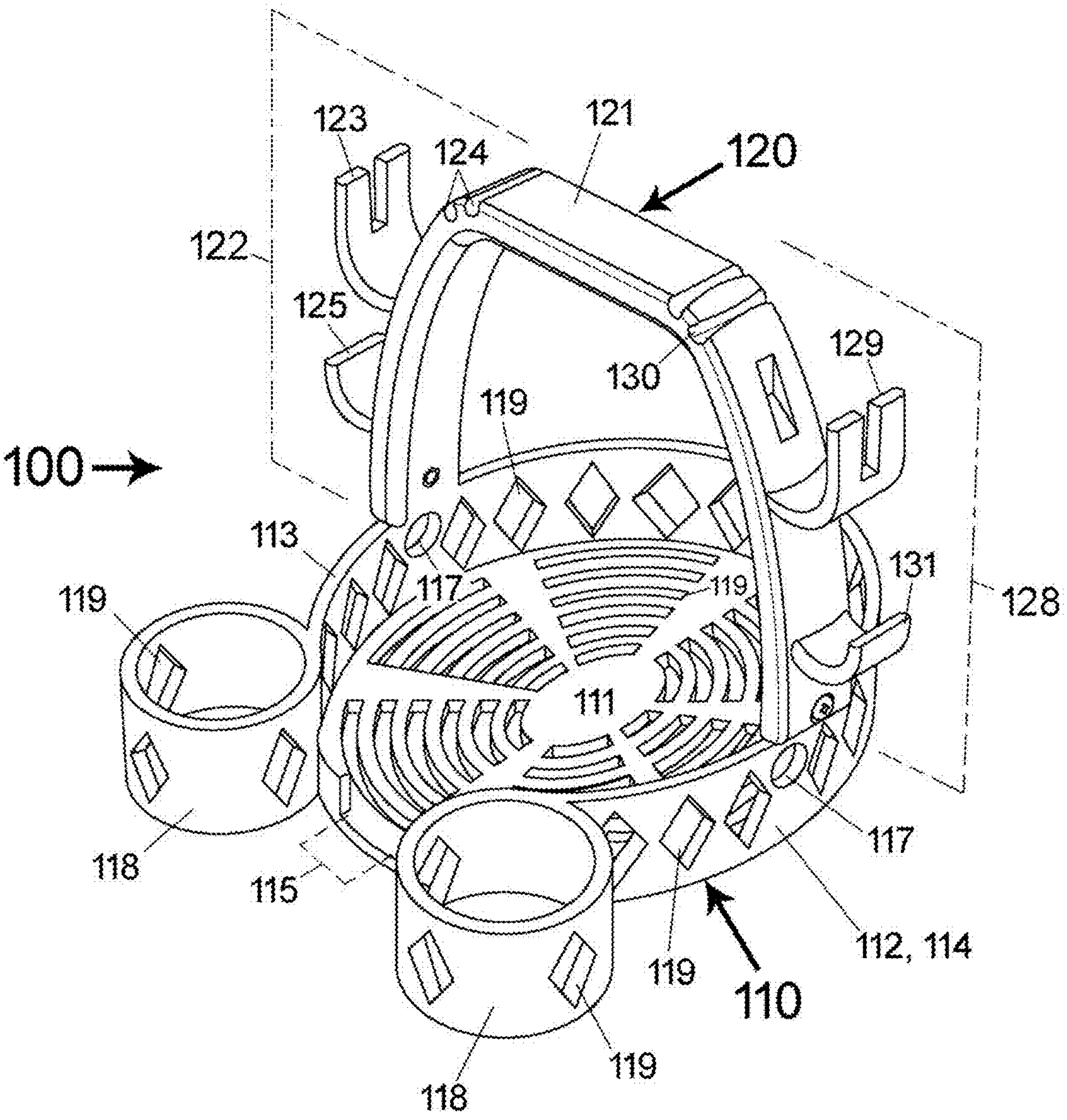
FIG. 2 is a right perspective view of the fully assembled breast pump caddy assembly, using descriptive key numbers to outline the locations and interconnectivity of components. The primary components include the caddy base and caddy handle. The figure utilizes these key numbers to indicate the precise positioning of various sub-components, including: bottom plate, wall, top surface, external surface, tubing inlet, plurality of power cord portals, two bottle holders, and plurality of weight cutouts. The handle sub-components are: handle grip, left handle brace, left cap hook, left tubing notches, left shield hook, right handle brace, right cap hook, right tubing notches, and right shield hook; in accordance with an exemplary embodiment of the present invention.

As shown in FIG. 2, the caddy base 110 comprises of a bottom plate 111, wall 112 (having a top surface 113, an external surface 114, a tubing inlet 115, two mounting blocks 116, plurality of power cords portals 117, and a plurality of weight cutouts) and two bottle holders 118. The wall 112 is attached to the periphery of the bottom plate 111, and extends upwardly forming a basket-like shape, designed to securely house the electric breast pump 201, preventing any movement.

Figure 4:
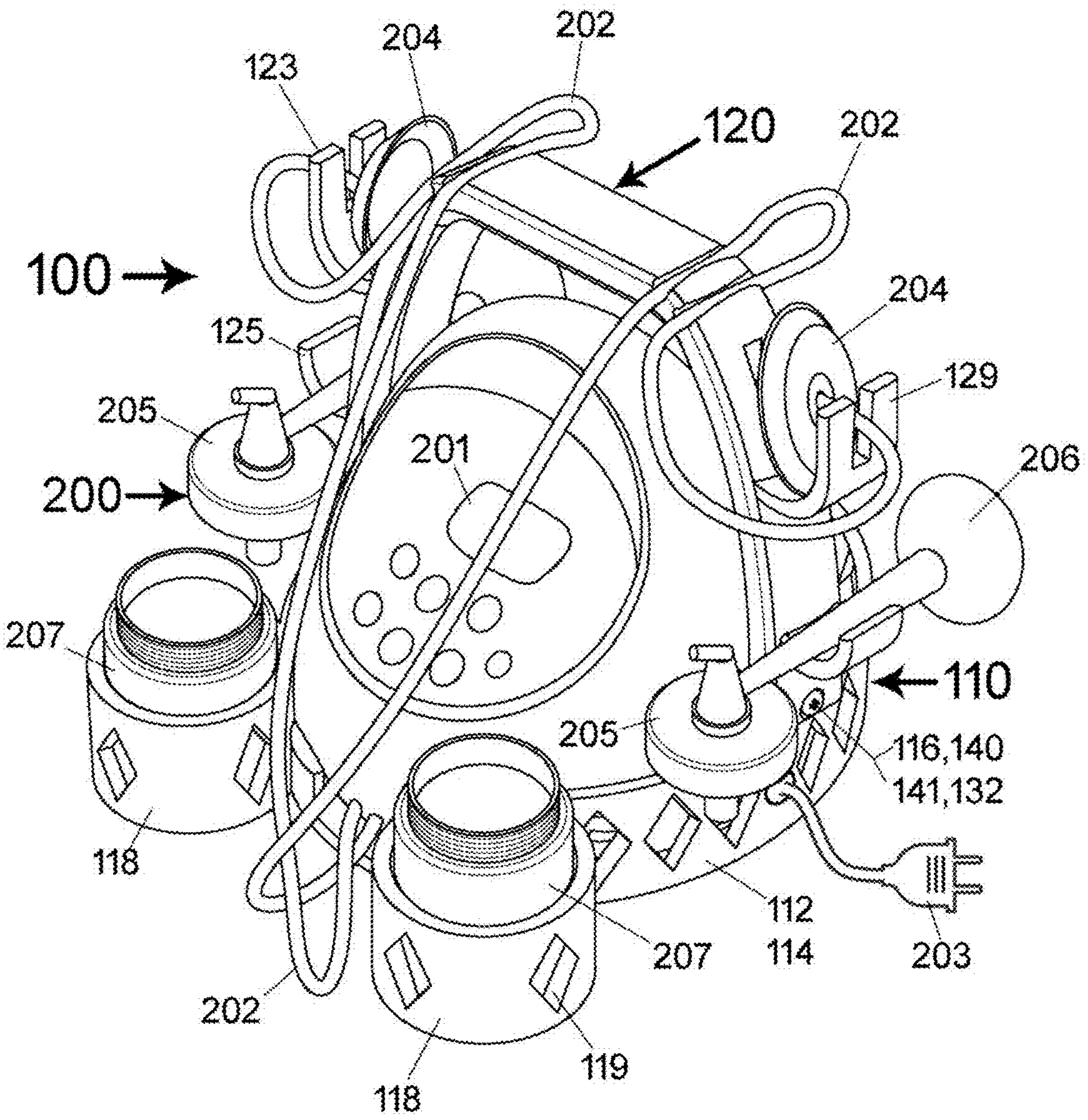
FIG. 4 is a right perspective view of the breast pump caddy assembly housing the breast pump assembly. In this figure: (1) The electric breast pump (containing the motor) is situated inside a basket-like shape formed by the wall connection to the caddy base, preventing movement of the electric breast pump. (2) The tubing connecting the electric breast pump to the top backflow caps is routed through the tubing inlet and held by the left and right tubing notches. (3) The two breast milk collection bottles are situated inside the two bottle holders. (4) The top backflow caps are held by the left and right cap hooks. (5) The two breast shields, each connecting to one of the two bottom backflow caps, are held by the left and right shield hooks; in accordance with an exemplary embodiment of the present invention.

Once the electric breast pump 201 is housed inside the caddy base 110, the pump 201 can be utilized immediately or remain inside the Caddy 100, in which case the Caddy 100 serves as a storage unit that can be moved to another location at any time. This means that the breast pump assembly 200 does not have to be removed from the Caddy 100 when in use, as the power cord 203 of the electric breast pump 201 can be plugged in or unplugged via the plurality of power cord portals 117, as shown in FIG. 4.

The caddy handle 120 comprises of three main components, namely the handle grip 121, left handle brace 122 and the right handle brace 128. The left handle brace 122 incorporates the left cap hook 123, left tubing notches 124 (positioned between the handle grip 121 and the left cap hook 123) and the left shield hook 125 positioned directly beneath the left cap hook 123. The right handle brace 128 incorporates the right cap hook 129, right tubing notches 130 (positioned between the handle grip 121 and the right cap hook 129) and the right shield hook 131 positioned directly beneath the right cap hook 129.

Figure 3:
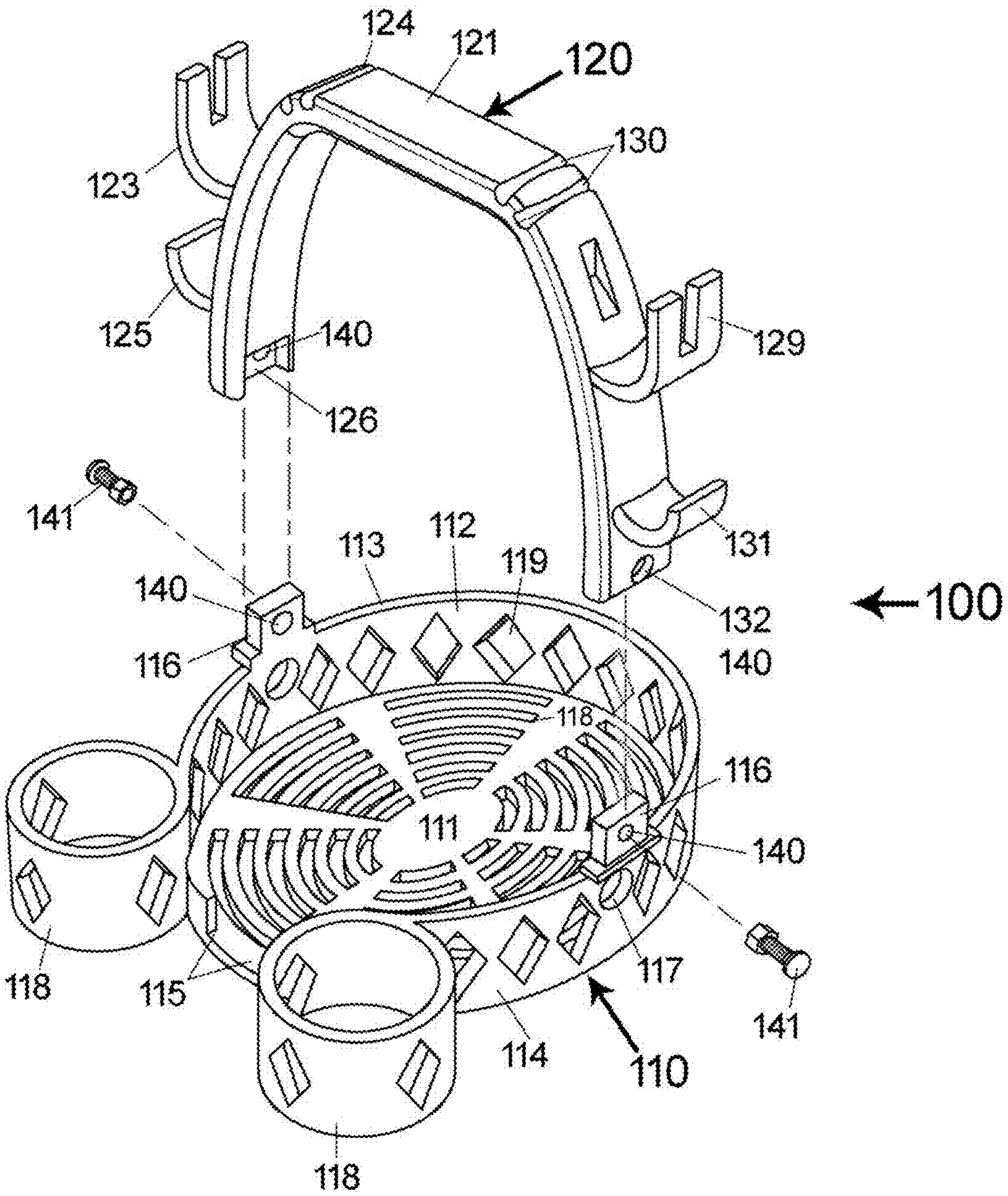
FIG. 3 is a right perspective exploded view of the breast pump caddy assembly, showing the caddy handle separated from the caddy base. This figure illustrates how the caddy handle is firmly attached to the caddy base using two mounting blocks designed to fit into the left and right connecting receptacles. These receptacles are then locked in place using mounting screws and corresponding nuts fitted through the mounting holes situated inside the left and right connecting receptacles; in accordance with an exemplary embodiment of the present invention.

As shown in FIG. 3, the caddy base 110 is securely attached to the caddy handle 120 using mounting screws and corresponding nuts 141 (either basic hex nuts or lock nuts). Specifically, the wall 112 of the caddy base 110 features two mounting blocks 116 attached to its top surface 113 and extending upward. These mounting blocks 116 are designed to fit snugly into the left 126 and right 132 connecting receptacles.

The mounting blocks 116, along with the left 126 and right 132 connecting receptacles, have corresponding mounting holes 140. The mounting screws and their corresponding lock nuts 141 are inserted through the mounting holes 140 to ensure a reliable connection. It is possible that either or both of these components (two mounting blocks 116 or left 126/right 132 connecting receptacles) may include a pocket to accommodate the head of the mounting screw or the corresponding nut.

As shown in FIG. 4, the left 124 and right 130 tubing notches are designed to hold tubing 202 that is routed from the electric breast pump 201 via the tubing inlet 115 to the top backflow caps 204. In this design, there are two top backflow caps 204. One top backflow cap 204 is stored on the left cap hook 123, which is positioned on the left handle brace 122, while the other top backflow cap 204 is stored on the right cap hook 129, located on the right handle brace 128. It is envisioned that other versions of the present invention may incorporate additional tubing notches to enable the organization of breast pumps with longer tubing.

The left 125 and right 131 shield hooks are designed to hold two breast shields 206 and two bottom backflow caps 205. In the current design, the breast shields 206 and bottom backflow caps 205 are connected together. However, future versions of the breast pump assembly may feature these components as separate pieces. In such cases, an updated version of the present invention would include an additional hook on the handle to accommodate the separate components.

Attached to the exterior surface 114 of the wall 112 are two bottle holders 118 designed to accommodate two breast milk collection bottles 207. This feature is highly practical for the Caddy 100, as it helps prevent spills. Often, milk collected in the bottles 207 can be accidentally spilled when the user attempts to manage multiple accessories after the collection process, particularly when the pump assembly 200 is placed on nearby flat surfaces. It is possible that alternative versions of the breast pump may incorporate additional breast milk collection bottles 207. If so, it is envisioned that a modified version of the present invention will include additional bottle holders 118, also attached to the exterior surface 114 of the wall 112.

I claim:

1. A breast pump caddy for holding, organizing and carrying a breast pump assembly, comprising:

(A) a caddy base configured for placing therein an electric breast pump of the breast pump assembly;

(B) a caddy handle;

(C) wherein the caddy base further comprises:

(a) a bottom plate;

(b) a wall having a top surface and an external surface;

(c) wherein said wall is extending upwardly from and enclosing the bottom plate;

(d) wherein said wall is configured to prevent movement of the electric breast pump placed on the caddy base;

(e) wherein said wall further comprises a tubing inlet for routing tubing extending from the electric breast pump to top backflow caps of the breast pump assembly;

(f) two mounting blocks fixedly disposed on the top surface of the wall;

(g) wherein said mounting blocks are extending upwardly from the wall and are configured to face each other;

(h) a plurality of power cord portals for routing through power cord extending from the electric breast pump;

(i) two bottle holders fixedly disposed on the external surface of the wall, each configured to hold one of two breast milk collection bottles;

(D) wherein the caddy handle further comprises:

(a) a handle grip for carrying the breast pump caddy;

(b) a left handle brace extending downwardly from the handle grip;

(c) a right handle brace extending downwardly from the handle grip;

(d) a left cap hook fixedly disposed on the left handle brace configured for holding one of said top backflow caps;

(e) left tubing notches disposed on the caddy handle between the handle grip and the left cap hook;

(f) wherein said left tubing notches are configured to releasably hold the tubing connecting the electric breast pump to the top backflow cap disposed on the left cap hook;

(g) a right cap hook fixedly disposed on the right handle brace configured for holding one of said top backflow caps;

(h) right tubing notches disposed on the caddy handle between the handle grip and the right cap hook;

(i) wherein said right tubing notches are configured to releasably hold the tubing connecting the electric breast pump to the top backflow cap disposed on the right cap hook;

(j) a left shield hook fixedly disposed on the left handle brace directly below the left cap hook;

(k) wherein said left shield hook is configured to releasably hold one of two breast shields and connected thereto one of two bottom backflow caps of the breast pump assembly;

(l) a right shield hook fixedly disposed on the right handle brace directly below the right cap hook;

(m) wherein said right shield hook is configured to releasably hold one of two breast shields and connected thereto one of two bottom backflow caps of the breast pump assembly;

(n) wherein said left handle brace further comprises a left connecting receptacle configured to accept one of the two mounting blocks, thereby connecting the left handle brace to the caddy base; and (o) wherein said right handle brace further comprises a right connecting receptacle configured to accept one of the two mounting blocks, thereby connecting the right handle brace to the caddy base;

whereby the connection between the wall and the caddy base creates a basket-like shape that secures the electric breast pump therein, preventing any movement, ensuring that the tubing connecting the electric breast pump to the top backflow caps remains unobstructed and organized using left using the left and right tubing notches, while other components of the breast pump assembly, such as breast milk collection bottles, top and bottom backflow caps, are organized and secured in place, allowing for use of the breast pump assembly without having to remove it from the breast pump caddy or to carry the breast pump assembly without the risk of losing any of its components.

2. The breast pump caddy for holding, organizing and carrying a breast pump assembly of claim 1, wherein: said tubing inlet is disposed between the two bottle holders.

3. The breast pump caddy for holding, organizing and carrying a breast pump assembly of claim 1, wherein: said caddy base further comprises a plurality of weight cutouts configured to reduce weight of the breast pump caddy.

4. The breast pump caddy for holding, organizing and carrying a breast pump assembly of claim 1, further comprising: mounting holes protruding through the two mounting blocks, left connecting receptacle, and right connecting receptacle.

5. The breast pump caddy for holding, organizing and carrying a breast pump assembly of claim 4, further comprising: mounting screws and corresponding nuts configured to fixedly attach the right connecting receptacle and the left connecting receptacle to the two mounting blocks via said mounting holes.

* * * * *